United States Patent [19]
Feldmann

[11] Patent Number: 5,717,996
[45] Date of Patent: Feb. 17, 1998

[54] SHIN AND ANKLE PROTECTION DEVICE

[76] Inventor: Dov Feldmann, 2A Itzhak Sade, 35251 Haifa, Israel

[21] Appl. No.: 634,459

[22] Filed: Apr. 18, 1996

[51] Int. Cl.[6] .................. A41D 13/00; A61F 5/00
[52] U.S. Cl. .................. 2/22; 2/455; 602/13; 602/23
[58] Field of Search ............... 2/24, 22, 16, 455; 602/20, 23, 13; 128/882, 892

[56] References Cited

U.S. PATENT DOCUMENTS

| | | | |
|---|---|---|---|
| 1,117,168 | 11/1914 | Crowley | 2/24 |
| 2,657,385 | 11/1953 | Cushman et al. | 2/24 |
| 3,351,055 | 11/1967 | Gottfried | 128/DIG. 20 |
| 4,266,298 | 5/1981 | Graziano | 602/13 |
| 4,378,009 | 3/1983 | Rowley et al. | 2/24 |
| 4,914,753 | 4/1990 | Chang | 2/24 |
| 5,060,641 | 10/1991 | Jones | 602/13 |
| 5,288,286 | 2/1994 | Davis et al. | 602/13 |
| 5,328,445 | 7/1994 | Spahn et al. | 602/23 |
| 5,435,009 | 7/1995 | Schlid et al. | 2/22 |
| 5,450,858 | 9/1995 | Zablotsky et al. | 602/13 |
| 5,524,292 | 6/1996 | Hargens | 2/24 |

FOREIGN PATENT DOCUMENTS

| 1491215 | 6/1970 | Germany | 602/13 |
|---|---|---|---|

*Primary Examiner*—Bibhu Mohanty
*Attorney, Agent, or Firm*—Mark M. Friedman

[57] ABSTRACT

A leg protection device for protecting the lower leg of a user from injury. The device includes a leg covering and an anterior air bag which is mounted in the leg covering. The anterior air bag includes a series of vertically extending chambers which are interconnected so as to equalize pressure among the chambers, thereby serving to spread the impact of a sharp impact and thereby reducing the chances for injury. The device may also include a shield adjacent the air bag and may also include a posterior air bag for protecting the Achilles tendon and related structures at or near the user's ankle.

20 Claims, 3 Drawing Sheets

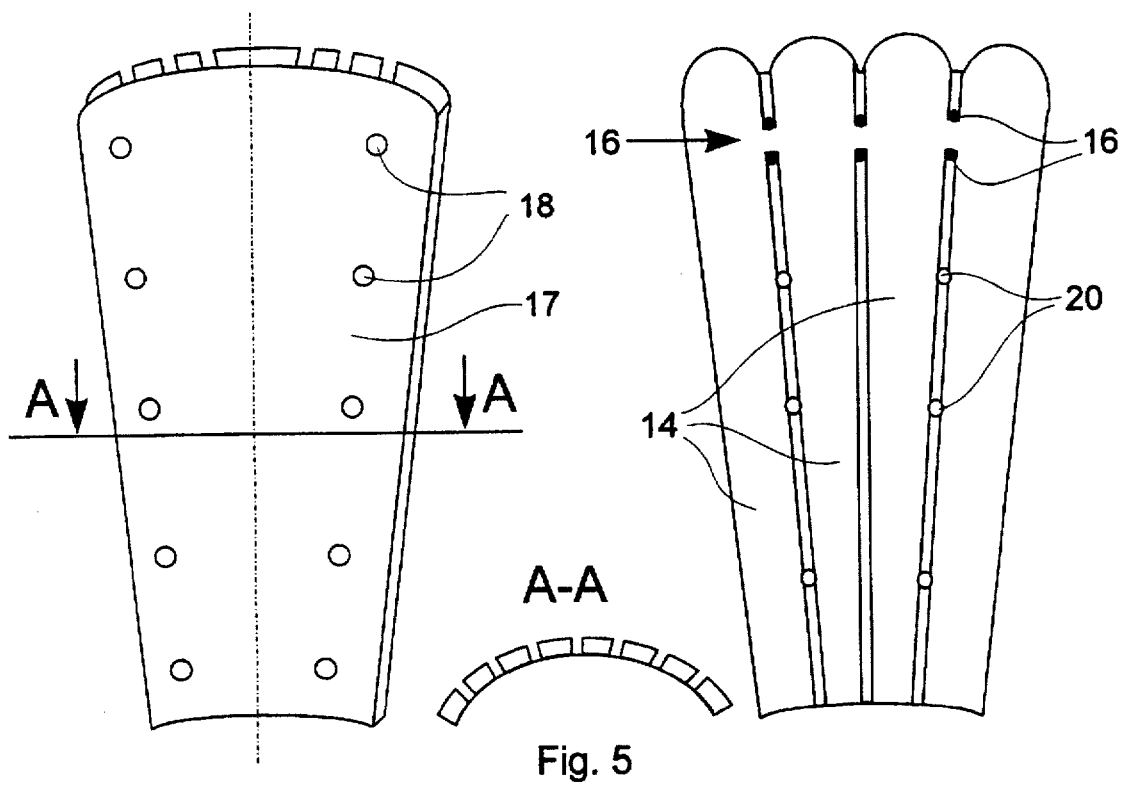

SHIN AND ANKLE PROTECTION DEVICE

FIELD AND BACKGROUND OF THE INVENTION

The present invention relates to devices for protecting the leg and, more particularly, to devices which may be worn on the leg to protect against leg injuries to the bones, muscles, tendons, blood vessels, and other soft tissues, as might occur during sporting activities, such as soccer or football.

A wide variety of means designed to protect the legs from injury are presently available. These range from bandages which are wrapped around the ankle to rigid plastic structures which are suitable mounted onto the leg.

Protection device in use today, while not adversely affecting the user's mobility, are largely ineffective against a sharp and highly localized impact, such as might be experienced, for example, when the leg is kicked with great force by the point of the shoe of a soccer or football player.

None of the protection devices currently available provides effective protection of both the front and rear portions of the user's leg.

There is thus a widely recognized need for, and it would be highly advantageous to have, a device for protecting the leg of a user from impacts which might otherwise injure the user's bones, muscles, tendons, and other tissues, while not adversely affecting the user's mobility and performance.

SUMMARY OF THE INVENTION

According to the present invention there is provided a leg protection device for protecting a leg of a user from injury, comprising: (a) a leg covering; (b) an anterior air bag associated with said leg covering, said anterior air bag characterized in that it includes a series of substantially vertically extending anterior chambers, said anterior chambers being interconnected so as to equalize pressure among said anterior chambers.

According to further features in preferred embodiments of the invention described below, the device further comprises an anterior shield adjacent the anterior air bag.

According to still further features in the described preferred embodiments, the device further comprises a posterior air bag associated with said leg covering, said posterior air bag characterized in that it includes a series of substantially vertically extending posterior chambers, said posterior chambers being interconnected so as to equalize pressure among said posterior chambers.

The present invention successfully addresses the shortcomings of the presently known configurations by providing a leg protector which may be worn like a knee sock and which effectively protects the leg of the user from sharp impacts which might otherwise injure the user's bones, tendons, nerves and other tissue, while not adversely affecting the user's mobility and performance.

BRIEF DESCRIPTION OF THE DRAWINGS

The invention is herein described, by way of example only, with reference to the accompanying drawings, wherein:

FIG. 3 is a front view of an anterior air pad which forms a part of a leg protector of the present invention;

FIG. 4 is a front view of a shield which forms a part of a preferred embodiment of a leg protector of the present invention;

FIG. 5 is a cross-sectional view along the section lines A—A of FIG. 4;

DESCRIPTION OF THE PREFERRED EMBODIMENTS

The present invention is of a lower leg protector which can be used to protect a user's shins and ankle, including bones, tendons, blood vessels and other tissue from injury, especially during sporting activities such as during soccer and football competition.

The principles and operation of a leg protector according to the present invention may be better understood with reference to the drawings and the accompanying description.

Figures 1, 2:
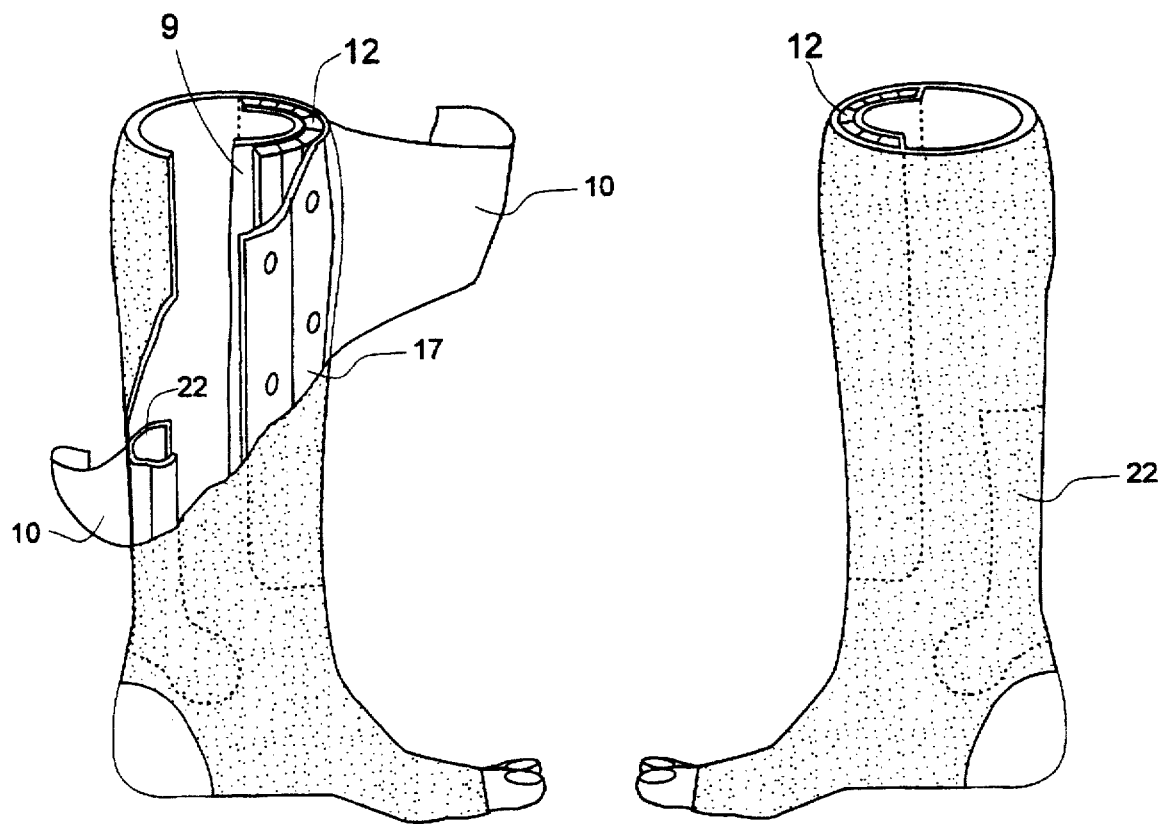
FIG. 1 is a side view of a leg protector according to the present invention.
FIG. 2 is a side view of the leg protector of FIG. 1 but with portions of the device partially cut away to expose some of the components of the device.

Referring now to the drawings, FIG. 1 illustrates a typical leg protector according to the present invention.

The protector includes a leg covering 10 which is preferably shaped like a knee sock and is donned in the same way as one would put on a knee sock. Preferably, leg covering 10 is made of an elastic material to ensure that it snugly wraps about the user's leg. As shown in FIG. 2, leg covering, designated as 9 and 10, is typically an elastic knee sock having dual walls which may, in practice be made up of two separated sock members—one of which (9) is worn directly on the user's lower leg, as would a conventional knee sock, while the other (10), which may be substantially identical to the first, is worn over the first and represents the outer layer of the protection device. The two sock members are constructed so as to form one or more pouch of suitable proportions into which can be placed the anterior air bag and shield and the posterior air bag, as described in more detail below. The function of the dual layered leg covering 10.

The protector further includes an anterior air bag 12 which is associated with leg covering 10 such that anterior air bag 12 is held snugly against the front of the wearer's leg. The approximate outline of anterior air bag 12 is shown by a broken line in FIG. 1. A portion of anterior air bag is shown in the partial cutaway view of FIG. 2. Air bag 12 may be made of any suitable material which is sufficiently non-porous as to retain the enclosed air and sufficiently flexible to bend somewhat with motion of the leg. Various plastic materials are preferred, for example polyurethane.

As can best be seen in FIG. 3, anterior air bag 12 is characterized in that it includes a series of substantially vertically extending anterior chambers 14 which are interconnected through air passages 16 so as to equalize the air pressure in all anterior chambers 14. This property of anterior air bag 12 makes it possible to effectively blunt the impact of a sharp kick, as by the front of an opposing player's shoe and helps spread the force of the kick over a much larger area, thereby significantly reducing, or even completely eliminating, the potential for damage of the leg.

The use of a series of vertical chambers 14 makes it possible for air bag 12 to be mounted so that it takes on the contour of the front of the user's leg. The cross-sectional view of FIG. 5 demonstrates how anterior air bag 12 curves to fit around the user's leg. Air bag 12 is preferably manufactured as a flat item and its construction makes it possible to readily bend air bag 12 around the leg of the user.

The use of interconnected chambers 14 serves to spread any impact experienced to a large portion of the user's leg.

The most serious sports leg injuries result from sharp impact to the leg, as by the toe of an opposing player's shoe. The delivery of such a large force onto a relatively small area puts tremendous pressure on the underlying tissue and could lead to damage to bones, muscles, tendons, blood vessels and other soft tissues.

The air-filled air bag 12 absorbs the sharp impact and spreads it almost instantaneously throughout air bag 12 so that, while substantially the same force is ultimately delivered to the leg, the force is spread over a much larger area, thereby greatly reducing the pressure at any particular point and greatly reducing the chance of serious injury.

Preferably, adjacent anterior air bag 12 is an anterior shield 17, which may be semi-rigid and which is preferably made of a suitable plastic, such as, for example, acetate. Most preferably, anterior shield 17 is located outwardly from air bag 12 so that air bag 12 is located between anterior shield 17 and the user's leg. The function of anterior shield 17 is to help spread the sharp impact onto substantially all chambers 14 of anterior air bag 12.

Preferably, anterior shield 17 includes a plurality of shield openings 18 therethrough to allow air to flow between the user's leg and the surroundings, thereby enhancing the user's comfort. Air bag 12 also preferably includes a series of air bag openings 20 therethrough (FIG. 3) to ensure unimpeded passage of air to and from the user's leg and for allowing sweat from the leg to escape, thereby increasing the comfort of the user.

Figure 6:
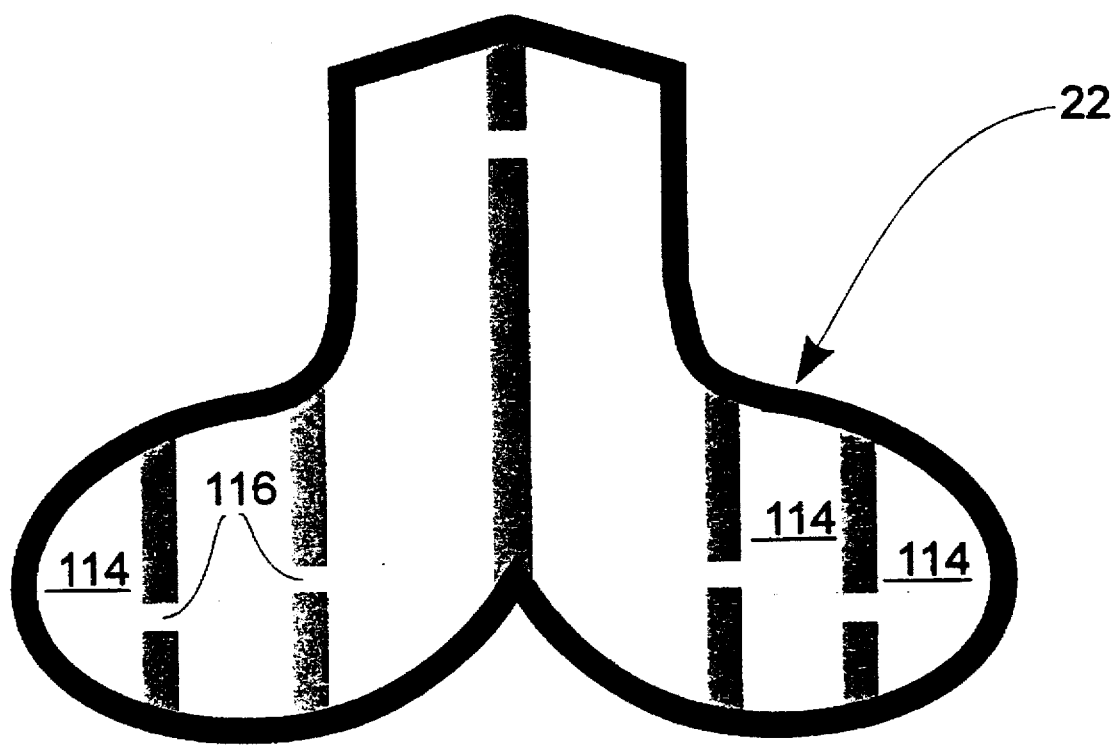
FIG. 6 is a cross-sectional view of a posterior air pad which forms a part of a preferred embodiment of a leg protector according to the present invention.

Preferably, a leg protector further includes a posterior air bag 22 which is designed to protect the calcaneal (Achilles) tendon, the peroneus brevis and longus tendons, and similar structures at the back end of the leg. A preferred shape of posterior air bag 22 is shown in FIG. 6. Posterior air bag 22 is similar to anterior air bag 12 in that it is made up of a plurality of substantially vertical chambers 114 which are interconnected through a number of air passages 116.

While the invention has been described with respect to a limited number of embodiments, it will be appreciated that many variations, modifications and other applications of the invention may be made.

What is claimed is:

1. A leg protection device for protecting a leg of a user from injury, comprising:
   (a) a leg covering;
   (b) an anterior air bag associated with said leg covering, said anterior air bag characterized in that it includes a series of substantially vertically extending anterior chambers, said anterior chambers being interconnected so as to gradually equalize pressure among said anterior chambers; and
   (c) a posterior air bag associated with said leg covering, said posterior air bag characterized in that it includes a series of substantially vertically extending posterior chambers, said posterior chambers being interconnected so as to gradually equalize pressure among said posterior chambers.

2. The device of claim 1, further comprising an anterior shield adjacent said anterior air bag.

3. The device of claim 2, wherein said anterior shield is made of acetate.

4. The device of claim 1, wherein said anterior air bag is made of polyurethane.

5. The device of claim 1, wherein said posterior air bag is made of polyurethane.

6. The device of claim 1, wherein said leg covering is shaped like a sock.

7. The device of claim 1, wherein said leg covering is elastic.

8. The device of claim 1, wherein said anterior air bag includes at least one opening for ventilation of the leg of the user.

9. A leg protection device for protecting a leg of a user from injury, comprising:
   (a) a leg covering;
   (b) an anterior air bag associated with said leg covering, said anterior air bag characterized in that it includes a series of substantially vertically extending anterior chambers, said anterior chambers being interconnected so as to gradually equalize pressure among said anterior chambers; and
   (c) an anterior shield adjacent to said anterior air bag.

10. The device of claim 9, further comprising a posterior air bag.

11. The device of claim 9, wherein said anterior shield is made of acetate.

12. The device of claim 9, wherein said anterior air bag is made of polyurethane.

13. The device of claim 9, wherein said leg covering is shaped like a sock.

14. The device of claim 9, wherein said leg coveting is elastic.

15. A leg protection device for protecting a leg of a user from injury, comprising:
   (a) a leg covering;
   (b) a posterior air bag associated with said leg covering, said posterior air bag characterized in that it includes a series of substantially vertically extending posterior chambers, said posterior chambers being interconnected so as to gradually equalize pressure among said posterior chambers; and
   (c) a posterior shield adjacent to said posterior air bag.

16. The device of claim 15, wherein said anterior shield is made of acetate.

17. The device of claim 15, wherein said anterior air bag is made of polyurethane.

18. The device of claim 15, wherein said leg covering is shaped like a sock.

19. The device of claim 15, wherein said leg covering is elastic.

20. The device of claim 15, wherein said anterior air bag includes at least one opening for ventilation of the leg of the user.

* * * * *